United States Patent [19]

Martinez et al.

[11] Patent Number: 5,061,257
[45] Date of Patent: Oct. 29, 1991

[54] APERTURED, REINFORCED CATHETER

[75] Inventors: Mario J. Martinez; Jeffrey G. Gold, both of Miami; Kevin F. Hahnen, Miramar, all of Fla.

[73] Assignee: Cordis Corporation, Miami Lakes, Fla.

[21] Appl. No.: 516,458

[22] Filed: Apr. 30, 1990

[51] Int. Cl.⁵ .............................................. A61M 25/00
[52] U.S. Cl. .................................................... 604/282
[58] Field of Search ...................... 604/282, 280–281, 604/264; 128/658

[56] References Cited

U.S. PATENT DOCUMENTS

| 2,268,321 | 12/1941 | Flynn | 604/282 |
| 2,407,929 | 4/1946 | Jeckel | 604/282 |
| 3,485,234 | 12/1969 | Stevens | 604/281 |
| 3,498,286 | 3/1970 | Polanyi et al. | 604/282 |
| 3,924,632 | 12/1975 | Cook | 604/282 |
| 4,306,563 | 12/1981 | Iwatschenko | 604/282 |
| 4,425,919 | 1/1984 | Alston, Jr. et al. | 604/282 |
| 4,639,252 | 1/1987 | Kelly et al. | 604/282 |
| 4,657,024 | 4/1987 | Coneys | 128/658 |
| 4,817,613 | 4/1989 | Jaraczewski et al. | 604/282 |
| 4,842,590 | 6/1989 | Tanabe et al. | 604/202 |
| 4,990,143 | 2/1991 | Sheridan | 604/282 |

FOREIGN PATENT DOCUMENTS 1199761 1/1986 Canada .
2043201 2/1979 United Kingdom .

Primary Examiner—C. Fred Rosenbaum
Assistant Examiner—Mark Bockelman
Attorney, Agent, or Firm—Gerstman & Ellis, Ltd.

[57] ABSTRACT

A catheter defines a flexible, tubular body in which the tubular body carries a tubular reinforcing sleeve made of strands. By this invention the catheter defines at least one side hole which communicates through the tubular body and tubular reinforcing sleeve. Greater resistance against collapse is thus provided to the section of the catheter which defines the side hole or preferably side holes.

18 Claims, 1 Drawing Sheet

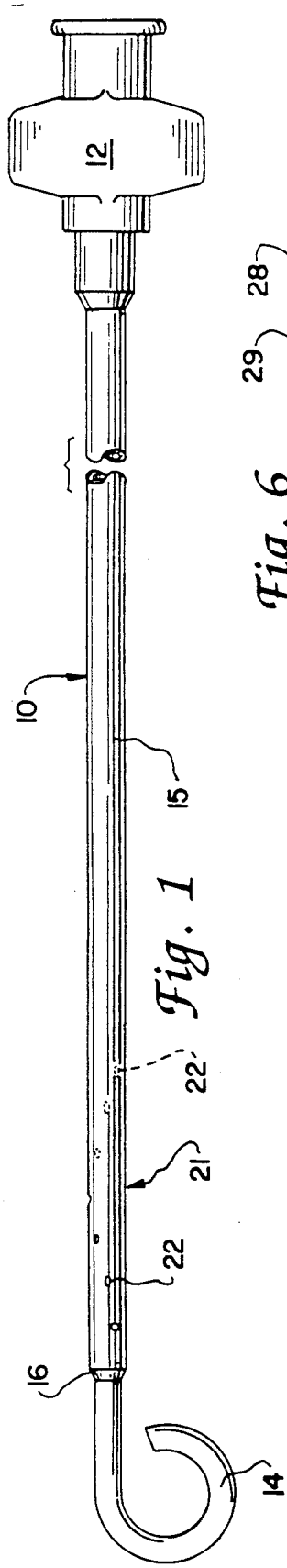

APERTURED, REINFORCED CATHETER

BACKGROUND OF THE INVENTION

Catheters such as angiographic catheters are generally reinforced with internal tubular reinforcing sleeves which are typically made of woven or otherwise spirally arranged crossing strands, typically made of metal. Such angiographic catheters are currently used in a variety of clinical procedures in which a fluid, particularly x-ray contrast media, is injected through the catheter into a blood vessel of the body leading to and from the heart for use in flush studies and ventriculograms. To accomplish this, angiographic catheters are frequently threaded through the aorta and the heart itself, to pass through the aortic valve for x-ray imaging of the heart ventricle or the like.

Many designs of angiographic catheters are known. However, typically, the currently preferred designs of angiographic catheters for flush studies or ventriculograms are so-called "pigtail" catheters, in which the distal tip of the catheter defines a loop, which facilitates the entry of the distal tip of the catheter through the aortic valve without causing any damage. However, straight catheters may also be used for similar purposes.

Also, as shown for example in Ruiz U.S. Pat. No. 4,573,476, the distal end of an angiographic catheter may define side holes for the lateral outflow of x-ray contrast fluid or the like, along with a longitudinal, distal exit for the catheter lumen, so that this fluid is delivered out of the distal end of the catheter in longitudinal manner.

The purpose of the typically-braided metal strand tubular reinforcing member is to increase the stiffness and strength of the catheter tubular body, to facilitate push-advancement of the catheter through the vascular system of the patient. In the prior art, the braided metal strand tubular reinforcing sleeve is absent from the distal tip area of the catheter where the side holes reside, and is also absent in the pigtail area distal to the side holes. Accordingly, the tip area is of less strength than the main body of the catheter which carries the tubular reinforcing sleeve. As a result of this, complaints have arisen as to some currently available angiographic catheters from surgeons, who have reported that in clinical use, as they have attempted to put the pigtail tip through the aortic valve, the distal tip area in which the side holes reside sometimes buckles. This of course is quite undesirable.

In accordance with this invention, an improved catheter is provided, which may be used as a angiographic catheter, and which reduces or eliminates the buckling problem of the side hole area in the tip. At the same time, the catheter may be manufactured with improved facility and simplicity, resulting in a reduction of the manufacturing cost and the consequent overall cost of the catheter, when compared with previous designs.

DESCRIPTION OF THE INVENTION

In accordance with this invention a catheter is provided which defines a flexible, tubular body in which the tubular body carries a tubular reinforcing sleeve made of crossing strands, typically metal strands, but, if desired, appropriate plastic strands may be used as well.

In accordance with this invention, the catheter defines at least one side hole which communicates through the tubular body and the tubular reinforcing sleeve. Preferably, a plurality of side holes are provided which communicate through the tubular body and reinforcing sleeve. By this invention, the area of the catheter which defines the side holes is reinforced by the presence of the tubular reinforcing sleeve, to control undesired collapsing of that section of the catheter.

In one embodiment of the catheter of this invention, the strands of the tubular reinforcing sleeve can extend across the side holes. In other words, only the flexible, typically plastic material of the tubular body is removed, to define the side holes with the tubular reinforcing sleeve extending across, it rather like a screen in an open window. This has the added advantage of providing a safety mesh across the aperture so that the reinforcing sleeve not only serves to reinforce the catheter, but prevents accidental exit of a guide wire within the catheter out of the side hole.

Alternatively, the side holes may be free of the strands of the reinforcing sleeve, with both the plastic material and the strands being cut away by a punching process, for example, so that the side holes are fully open. In either case the side holes are open and capable of fluid flow since, even if the reinforcing sleeve is present, the strands are separated by interstices, and thus permit fluid flow with ease.

It is generally preferred for the catheter to also carry a distal tip which is free of the reinforcing sleeve. Typically, this is a "pigtail" tip of reduced diameter, when compared with the rest of the catheter.

It may be desired for the tubular body of the catheter to define an inner, extruded plastic layer, with the tubular reinforcing sleeve surrounding and usually adhering to the inner, extruded layer. Also, an outer, extruded plastic layer is provided, surrounding and usually adhering to the tubular reinforcing sleeve. The distal tip, in this circumstance, may comprise a portion of the inner, extruded plastic layer which is substantially free from the outer plastic layer, as well as the reinforcing sleeve, extending distally beyond them both.

By this invention, which in one aspect involves the extension of the tubular reinforcing sleeve through the portion of the catheter that defines the side holes, a whipping action that is sometimes apparent in catheters subjected to high pressure flow of contrast media can be minimized or eliminated.

The punching of the side holes in the tip through the catheter wall and optionally the tubular reinforcing sleeve may be accomplished by use of a laser, directed, superheated steam, hot media injected at high pressure, particle bombardment, radio frequency treatment, hot probes, or any other mechanical means. As desired, the strands of the reinforcing sleeve may either be allowed to remain extending across the side holes, or they may be removed, as desired.

A soft tip may be provided to the catheter of this invention. For example, the inner, extruded plastic layer may be made of a relatively soft material, (for example 50 Durometer polyurethane elastomer) compared with a harder plastic material used for the outer, extruded plastic layer, such as 55 Durometer polyurethane elastomer. Accordingly, the main catheter body will have a relatively hard and stiff feel, while retaining a desired degree of flexibility, when compared with the soft tip made of the inner, extruded layer, free of the tubular reinforcing sleeve and stiffer plastic: outer extruded layer. Alternatively, the catheter may be ground away adjacent the soft distal tip to remove a possibly-harder outer plastic layer or top coat to expose the inner plastic layer as a soft tip. Alternatively, a preformed tip made of relatively soft material may be bonded to the rest of the catheter by conventional means, or the tip can be built up by a deposition of material by spray coating or dipping. Thus, a relatively stiff but flexible catheter may carry a substantially softer distal tip, particularly a "pigtail tip", to minimize trauma caused by insertion of the catheter.

DESCRIPTION OF THE DRAWINGS

In the drawings, FIG. 1 is a plan view of a pigtail-type angiographic catheter made in accordance with this invention;

FIG. 2 is an enlarged, plan view, with portions taken in longitudinal section, of a segment of the catheter of FIG. 1;

FIG. 3 is a sectional view taken along line 3—3 of FIG. 2;

FIG. 4 is a further-enlarged perspective view of a side hole of the catheter of FIG. 2, showing how the strands of the tubular reinforcing sleeve extend across the side hole;

FIG. 5 is a view similar to FIG. 4, but of another embodiment in which the strands of the reinforcing sleeve extending across the side hole have been removed; and FIG. 6 is a fragmentary, longitudinal sectional view of a modification of the catheter of FIG. 2.

DESCRIPTION OF SPECIFIC EMBODIMENTS

Referring to the drawings, angiographic catheter 10 is generally of the design of present, commercially available angiographic catheters except for the differences described herein Catheter 10 may typically be made of any appropriate flexible plastic material such as polyurethane, defining a proximal hub 12 of conventional design, a flexible, tubular body 15, and a distal pigtail tip 14, which also may be generally conventional except as otherwise indicated herein Tubular pigtail tip 14 may be heat sealed at heat seal site 16 to the distal end of the flexible tubular body 15. It can be seen that the width of lumen 18 of pigtail tip 14 may be less than the ∷width of lumen 20 of catheter body 15. It can also be seen that section 21 of the catheter, which defines side holes 22, may be an integral part of the catheter body 15 rather than a part of catheter tip 14, which is sealed to catheter body 15.

As shown, catheter body 15 carries a conventional tubular, braided metal fiber reinforcing sleeve 24 embedded in the wall of catheter body 15. Braided metal sleeve 24 can be seen to extend distally along the length of catheter body 15 at least substantially to seal area 16, where pigtail tip 14 is attached. In the embodiment shown in FIG. 3, strands of tubular reinforcing sleeve 24 extend across each of side holes 22 in the manner of a screen in an open window, the same configuration being shown in FIG. 4.

However, if desired, FIG. 5 shows an alternative embodiment in which the strands of tubular reinforcing sleeve 24 have been cut away in each side hole 22, so that the side hole is fully open.

Accordingly, the catheter made in accordance with this invention exhibits a side hole-defining section 21 which has substantially equal strength and resistance against collapse as the main portion of catheter body 15, so that the problem of collapse adjacent the side holes in clinical use may be avoided. At the same time, pigtail tip 14 may be substantially softer, being free of the reinforcing sleeve 24 and, if desired, being made of a softer plastic material than the plastic material of catheter body 15. Thus the distal tip of the catheter may be as soft and pliable as needed, to avoid tissue damage as the catheter is advanced through the vascular system of the patient or elsewhere.

Referring to FIG. 5, an alternate embodiment for the catheter tip is shown. It is conventional to extrude an inner plastic layer 26 of a catheter, followed by application of tubular reinforcing sleeve 28. Then, an outer plastic layer 30 may be applied over the inner layer 26 and reinforcing sleeve 28, and holes 29 formed as desired.

In accordance with this invention, inner plastic sleeve 26 may be of greater length than reinforcing sleeve 28 or outer plastic sleeve 30, to provide a distally projecting soft tip portion 32 which may be shaped into pigtail shape if desired. Clearly, soft tip portion 32 is more flexible than the composite of layers 26, 28, 30. Additionally, if desired, layer 26 may be made of a softer material than outer layer 28, to accentuate the relative softness of the distal tip portion 32 which can be produced in this manner. Distal tip portion 32 may be simply coextruded to be longer than the other layers 28, 30, or, alternatively, outer layer 28 may be later removed from distal tip portion 32, if desired.

Thus, a catheter is provided in which the area of the catheter that defines the side holes is reinforced by th presence of a section of the tubular reinforcing sleeve At the same time, a distal tip, which may be of the pigtail type, can remain soft and pliable. This can be accomplished if desired with a single, conventional sealing step between distal tip 14 and the distal end of catheter body 15. Alternatively, a corresponding distal tip portion 32 can be formed by a coextrusion technique as illustrated in FIG. 5.

The above has been offered for illustrative purposes only, and is not intended to limit the scope of the invention of this application, which is as defined in the claims below.

That which is claimed is:

1. In a catheter which defines a flexible, tubular body in which said tubular body carries a tubular reinforcing sleeve made of strands, the improvement comprising, in combination:

said catheter defining at least one side hole which communicates through said tubular body and strands of said tubular reinforcing sleeve, in which strands of said tubular reinforcing sleeve extend across said side hole.

2. The catheter of claim 1 in which a plurality of said side holes communicate through said tubular body and tubular reinforcing sleeve.

3. The catheter of claim 1 in which said strands of the tubular reinforcing sleeve are made of metal.

4. The catheter of claim 1 in which said catheter carries a distal tip free of said reinforcing sleeve.

5. The catheter of claim 4 in which said tubular body defines an inner, extruded plastic layer, said tubular reinforcing sleeve surrounding said inner, extruded layer, and an outer, extruded plastic layer surrounding said tubular reinforcing sleeve, said distal tip comprising a portion of said inner, extruded plastic layer extending from said outer layer and reinforcing sleeve in spaced relation.

6. In a catheter which defines a flexible, tubular body in which said tubular body carrier a tubular reinforcing sleeve made of crossing strands, the improvement comprising, in combination:

said catheter defining a plurality of side holes which communicate through the tubular body and tubular reinforcing sleeve, the strands of said tubular reinforcing sleeve extending across said side hole.

7. The catheter of claim 6 in which said catheter carriers a distal tip free of said reinforcing sleeve.

8. The catheter of claim 7 in which the strands of said tubular reinforcing sleeve are made of metal.

9. The catheter of claim 6 in which said tubular body defines an inner, extruded plastic layer, said tubular reinforcing sleeve surrounding and adhering to said inner, extruded layer, and an outer, extruded plastic layer surrounding and adhering to said tubular reinforcing sleeve, said distal tip comprising a portion of said inner, extruded plastic layer extending from and substantially free of said outer plastic layer and reinforcing sleeve.

10. The catheter of claim 9 in which said inner plastic layer is made of a material softer than said outer plastic layer.

11. In a catheter which defines a flexible, tubular body in which said tubular body carries a tubular reinforcing sleeve made of cross strands, the improvement comprising, in combination:

said catheter defining a plurality of side holes which communicate through said tubular body and strands of said tubular reinforcing sleeve, said side holes being free of said strands extending thereacross, in which said tubular body defines an inner, extruded plastic layer, said tubular reinforcing sleeve surrounding said inner, extruded layer, and an outer, extruded plastic layer surrounding said tubular reinforcing sleeve, said distal tip comprising a portion of said inner, extruded plastic layer extending from and substantially free of said outer plastic layer and reinforcing sleeve.

12. The catheter of claim 11 in which said catheter carrier a distal tip free of said reinforcing sleeve.

13. The catheter of claim 11 in which said inner, extruded plastic layer is made of a material substantially softer than the material of said outer plastic layer.

14. In a catheter which defines a flexible, tubular body in which said tubular body carries a tubular reinforcing sleeve made of strands; an inner, tubular plastic layer, said tubular reinforcing sleeve surrounding said inner plastic layer; and an outer, tubular plastic layer surrounding said tubular reinforcing sleeve; said catheter carrying a distal tip free of said reinforcing sleeve, said distal tip comprising an integral portion of said inner plastic layer extending distally from said outer plastic layer and reinforcing sleeve in spaced relation thereto.

15. The catheter of claim 14 in which the strands of said tubular reinforcing sleeve are made of metal.

16. The catheter of claim 14 in which a plurality of side holes communicate through said tubular body and tubular reinforcing sleeve.

17. The catheter of claim 16 in which strands of said tubular reinforcing sleeve extend across said 18. The catheter of claim 16 in which said side holes are free of strands extending thereacross.

* * * * *